United States Patent
Miyachi

(10) Patent No.: US 11,779,223 B2
(45) Date of Patent: Oct. 10, 2023

(54) IMAGE GENERATION APPARATUS AND OPERATION METHOD

(71) Applicant: FUJIFILM Corporation, Tokyo (JP)

(72) Inventor: Yukiya Miyachi, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 715 days.

(21) Appl. No.: 16/796,076

(22) Filed: Feb. 20, 2020

(65) Prior Publication Data

US 2020/0187783 A1    Jun. 18, 2020

Related U.S. Application Data

(63) Continuation of application No. PCT/JP2018/020264, filed on May 28, 2018.

(30) Foreign Application Priority Data

Aug. 31, 2017  (JP) .................. 2017-167899

(51) Int. Cl.
*G06T 7/00* (2017.01)
*A61B 5/00* (2006.01)
(Continued)

(52) U.S. Cl.
CPC .......... *A61B 5/0095* (2013.01); *A61B 5/6848* (2013.01); *A61B 5/7203* (2013.01);
(Continued)

(58) Field of Classification Search
CPC ......... G06T 5/002; G06T 7/0012; G06T 7/11; G06T 2207/10132; A61B 5/725; A61B 5/0095; A61B 2576/00
See application file for complete search history.

(56) References Cited

U.S. PATENT DOCUMENTS 5,933,540 A * 8/1999 Lakshminarayanan ......................
H04N 1/4092
382/128
9,943,231 B2 * 4/2018 Furukawa .......... G01N 29/2418
(Continued)

FOREIGN PATENT DOCUMENTS

| JP | 2008-264531 A | 11/2008 |
|---|---|---|
| JP | 2014-147825 A | 8/2014 |
| WO | WO 2016/051738 A1 | 4/2016 |

OTHER PUBLICATIONS

Japanese Office Action, dated Jan. 19, 2021, for Japanese Application No. 2019-538973, with an English translation.
(Continued)

*Primary Examiner* — Phi Hoang
(74) *Attorney, Agent, or Firm* — Birch, Stewart, Kolasch & Birch, LLP

(57) ABSTRACT

In a photoacoustic image generation apparatus including a photoacoustic image generation unit that generates a photoacoustic image based on a detection signal and a sound speed in a subject and a sound speed setting unit that sets the sound speed in the subject, the sound speed setting unit extracts a region having a predetermined range including a high signal value pixel collection portion having a region size larger than a reference region size as a tip region in a photoacoustic image generated based on an assumed sound speed and the detection signal and sets a sound speed of a photoacoustic image having a maximum image evaluation value as the sound speed in the subject among photoacoustic images for respective sound speeds generated by changing the sound speed in a predetermined sound speed range for the tip region.

17 Claims, 9 Drawing Sheets

(51) Int. Cl.
  *G06T 7/11* (2017.01)
  *G06T 5/00* (2006.01)
(52) U.S. Cl.
  CPC .............. *A61B 5/725* (2013.01); *G06T 5/002* (2013.01); *G06T 7/0012* (2013.01); *G06T 7/11* (2017.01); *A61B 2576/00* (2013.01); *G06T 2207/10132* (2013.01)

(56) References Cited

U.S. PATENT DOCUMENTS

| | | | |
|---|---|---|---|
| 2008/0242999 A1 | 10/2008 | Kakee | |
| 2015/0196274 A1* | 7/2015 | Yamamoto | G01S 15/8915 600/442 |
| 2015/0289839 A1* | 10/2015 | Saito | A61B 8/5215 600/424 |
| 2016/0007860 A1* | 1/2016 | Bates | A61B 5/6876 600/407 |
| 2016/0150973 A1* | 6/2016 | Abe | A61B 5/062 600/407 |
| 2017/0112465 A1* | 4/2017 | Takimoto | A61B 8/0833 |
| 2017/0196462 A1 | 7/2017 | Miyachi | |

OTHER PUBLICATIONS

Japanese Office Action, dated Jun. 22, 2021, for Japanese Application No. 2019-538973, with an English translation.
International Preliminary Report on Patentability and Written Opinion of the International Searching Authority (Forms PCT/IB/326, PCT/IB/373 and PCT/ISA/237) for International Application No. PCT/JP2018/020264, dated Mar. 12, 2020, with English translation.
International Search Report (Form PCT/ISA/210) for International Application No. PCT/JP2018/020264, dated Jul. 3, 2018, with English translation.

* cited by examiner

IMAGE GENERATION APPARATUS AND OPERATION METHOD

CROSS REFERENCE TO RELATED APPLICATIONS

This application is a Continuation of PCT International Application No. PCT/JP2018/020264 filed on May 28, 2018, which claims priority under 35 U.S.C § 119(a) to Patent Application No. 2017-167899 filed in Japan on Aug. 31, 2017, all of which are hereby expressly incorporated by reference into the present application.

BACKGROUND OF THE INVENTION

1. Field of the Invention

The present invention relates to an image generation apparatus that generates a photoacoustic image based on a detection signal acquired by detecting a photoacoustic wave emitted from a tip portion of an insert inserted into a subject using an acoustic wave detection means and an operation method of the image generation apparatus.

2. Description of the Related Art

An ultrasonography method has been known as a kind of image inspection method that can non-invasively inspect an internal state of a living body. An ultrasound probe that can transmit and receive ultrasonic waves is used in ultrasonography. In a case where the ultrasound probe transmits an ultrasonic wave to a subject (living body), the ultrasonic wave travels in the living body and is reflected from an interface between tissues. The ultrasound probe receives the reflected ultrasonic wave and a distance is calculated based on a time until the reflected ultrasonic wave returns to the ultrasound probe. In this manner, it is possible to capture an image indicating the internal state of the living body.

In addition, photoacoustic imaging has been known which captures an image of the inside of a living body using a photoacoustic effect. In general, the inside of the living body is irradiated with pulsed laser light in the photoacoustic imaging. In the inside of the living body, the living body tissue absorbs energy of the pulsed laser light and an ultrasonic wave (photoacoustic wave) is generated by adiabatic expansion caused by the energy. The ultrasound probe or the like detects the photoacoustic wave and a photoacoustic image is formed based on the detection signal. In this manner, it is possible to visualize the inside of the living body based on the photoacoustic wave.

In addition, a puncture needle provided with a photoacoustic wave generation portion that absorbs light and generates a photoacoustic wave near a tip thereof is proposed as a technique related to the photoacoustic imaging. In the puncture needle, an optical fiber is provided up to the tip of the puncture needle and light guided by the optical fiber is emitted to the photoacoustic wave generation portion. An ultrasound probe detects the photoacoustic wave generated by the photoacoustic wave generation portion, and a photoacoustic image is generated based on the detection signal of the photoacoustic wave. A portion of the photoacoustic wave generation portion appears as a bright point in the photoacoustic image. Therefore, it is possible to check a position of the puncture needle using the photoacoustic image.

SUMMARY OF THE INVENTION

In the photoacoustic imaging using the puncture needle as described above, it is necessary to accurately check a tip position of the puncture needle in the living body. Therefore, an image with particularly high resolution is required.

In a case where an image of the inside of the living body is captured using an ultrasonic wave (photoacoustic wave), the image is usually generated using an average sound speed in the living body. However, a sound speed in the living body is not constant and changes according to individual differences and sites. For this reason, there is a problem that the resolution of the image is degraded in a case where the sound speed used at a time of image generation is different from an actual sound speed.

In order to solve such a problem, a method for suppressing the degradation in image quality due to a mismatch between the sound speed used at the time of generating an ultrasound image and the actual sound speed has been proposed in the related art. Specifically, a sound speed correction method for setting a sound speed at which the brightness or contrast of an image is maximized among images for each sound speed generated by changing the sound speed in a conceivable range of sound speed in the living body for each pixel constituting the ultrasound image has been proposed as the sound speed at the time of capturing the image.

This sound speed correction processing requires a large amount of processing capability since it is necessary to generate the plurality of images and find the optimum sound speed for each pixel constituting the ultrasound image. JP2014-147825A discloses that a region having a predetermined range including a pixel having the highest brightness or contrast in an image is set as an interested region and the sound speed correction processing is performed only on the interested region. Accordingly, it is possible to reduce a load for the sound speed correction processing.

However, in the photoacoustic imaging using the puncture needle as described above, a pixel of a noise portion may have higher brightness or contrast than a pixel indicating the tip portion of the puncture needle in the photoacoustic image. Therefore, in a case where the region on which the sound speed correction is performed is determined by focusing on the pixel having the highest brightness or contrast in the image as in the technique disclosed in JP2014-147825A, there is a possibility that a tip region of the puncture needle that is desired to be most accurately checked in the photoacoustic image is out of the sound speed correction range and thus the resolution of the tip region of the puncture needle is reduced.

In view of the above circumstances, it is an object of the invention to provide an image generation apparatus that suppresses a reduction in resolution of a tip region of an insert in a photoacoustic image and an operation method of the image generation apparatus, in a case where sound speed correction is performed only on a partial region of the photoacoustic image for reducing a processing load in photoacoustic imaging using the insert such as a puncture needle.

An image generation apparatus according to an embodiment of the invention comprises a photoacoustic image generation unit that generates a photoacoustic image based on a detection signal acquired by detecting a photoacoustic wave emitted from a tip portion of an insert inserted into a subject using an acoustic wave detection means and a sound speed in the subject, and a sound speed setting unit that extracts a region having a predetermined range including a high signal value pixel collection portion having a region size larger than a reference region size as a tip region in a photoacoustic image generated based on an assumed sound speed and the detection signal, and sets a sound speed of a photoacoustic image having a maximum image evaluation value as the sound speed in the subject among photoacoustic images for respective sound speeds generated by changing the sound speed in a predetermined sound speed range for the tip region.

In the image generation apparatus according to the embodiment of the invention, the image evaluation value means an evaluation value for evaluating the image quality of the photoacoustic image. This image evaluation value indicates that the image quality becomes better as the evaluation value becomes higher. The image evaluation value may be, for example, an evaluation value indicating a smallness of intensity variation of a signal phase-adjusted based on sharpness of a photoacoustic image, contrast of the photoacoustic image, or a sound speed at a time of image generation in the tip region. This image evaluation value may be calculated based on pixel arrangements in both directions of the photoacoustic image in the lateral direction and the depth direction (vertical direction), may be calculated based on the pixel arrangement only in the lateral direction thereof, or may be calculated based on the pixel arrangement only in the depth direction (vertical direction) thereof. The sound speed correction in the image generation apparatus according to the embodiment of the invention is effective in improving the image quality particularly in the lateral direction of the lateral direction and depth direction (vertical direction) of the photoacoustic image. Therefore, it is preferable to calculate the image evaluation value of the photoacoustic image based on the pixel arrangement only in the lateral direction.

The reference region size may be adjusted based on a type of the insert, a generation condition of the photoacoustic wave, a type of the acoustic wave detection means, frequency characteristics of the acoustic wave detection means, a reception detection frequency band for the acoustic wave detection means, or a display size of a photoacoustic image.

The sound speed setting unit may specify a high signal value pixel collection portion having a region size larger than the reference region size by image recognition, and extract a region having a predetermined range including the extracted high signal value pixel collection portion as the tip region.

The sound speed setting unit may perform reduction processing of reducing signal intensity of a high signal value pixel collection portion having a region size smaller than the reference region size on the photoacoustic image generated based on an assumed sound speed and the detection signal, and extract a region having a predetermined range including a pixel having the highest signal value as the tip region in the photoacoustic image subjected to the reduction processing.

In this case, the reduction processing may be low pass filter processing having a half-width of 0.5 times or more to 2 times or less the reference region size, or may be smoothing filter processing.

In a case where the reduction processing is the smoothing filter processing, in the smoothing filter processing, a smoothing effect in a depth direction is preferable to be larger than a smoothing effect in a lateral direction in the photoacoustic image.

An operation method of an image generation apparatus according to an embodiment of the invention includes a photoacoustic image generation unit that generates a photoacoustic image based on a detection signal acquired by detecting a photoacoustic wave emitted from a tip portion of an insert inserted into a subject using an acoustic wave detection means and a sound speed in the subject, and a sound speed setting unit that sets the sound speed in the subject. The method comprises, by the sound speed setting unit, extracting a region having a predetermined range including a high signal value pixel collection portion having a region size larger than a reference region size as a tip region in a photoacoustic image generated based on an assumed sound speed and the detection signal, and setting a sound speed of a photoacoustic image having a maximum image evaluation value as the sound speed in the subject among photoacoustic images for respective sound speeds generated by changing the sound speed in a predetermined sound speed range for the tip region.

In the operation method of the invention, the image evaluation value may be an evaluation value indicating a smallness of intensity variation of a signal phase-adjusted based on sharpness of a photoacoustic image, contrast of the photoacoustic image, or a sound speed at the time of image generation in the tip region.

The reference region size may be adjusted based on a type of the insert, a generation condition of the photoacoustic wave, a type of the acoustic wave detection means, frequency characteristics of the acoustic wave detection means, a reception detection frequency band for the acoustic wave detection means, or a display size of a photoacoustic image.

The sound speed setting unit may specify a high signal value pixel collection portion having a region size larger than the reference region size by image recognition, and extract a region having a predetermined range including the extracted high signal value pixel collection portion as the tip region.

The sound speed setting unit may perform reduction processing of reducing signal intensity of a high signal value pixel collection portion having a region size smaller than the reference region size on the photoacoustic image generated based on an assumed sound speed and the detection signal, and extract a region having a predetermined range including a pixel having the highest signal value as the tip region in the photoacoustic image subjected to the reduction processing.

In this case, the reduction processing may be low pass filter processing having a half-width of 0.5 times or more to 2 times or less the reference region size, or may be smoothing filter processing.

In a case where the reduction processing is the smoothing filter processing, in the smoothing filter processing, a smoothing effect in a depth direction is preferable to be larger than a smoothing effect in a lateral direction in the photoacoustic image.

In an image generation apparatus comprising a photoacoustic image generation unit that generates a photoacoustic image based on a detection signal acquired by detecting a photoacoustic wave emitted from a tip portion of an insert inserted into a subject using an acoustic wave detection means and a sound speed in the subject and a sound speed setting unit that sets the sound speed in the subject, the image generation apparatus and the operation method according to the invention cause the sound speed setting unit to extract a region having a predetermined range including a high signal value pixel collection portion having a region size larger than a reference region size as a tip region in a photoacoustic image generated based on an assumed sound speed and the detection signal and to set a sound speed of a photoacoustic image having a maximum image evaluation value as the sound speed in the subject among photoacoustic images for respective sound speeds generated by changing the sound speed in a predetermined sound speed range for the tip region such that the tip region of the insert is appropriately selected as a range for the sound speed correction in a case where the sound speed correction is performed only on a partial region of the photoacoustic image for reducing the processing load. Therefore, it is possible to suppress the reduction in resolution of the tip region of the insert in the photoacoustic image.

DESCRIPTION OF THE PREFERRED EMBODIMENTS

Figure 1:
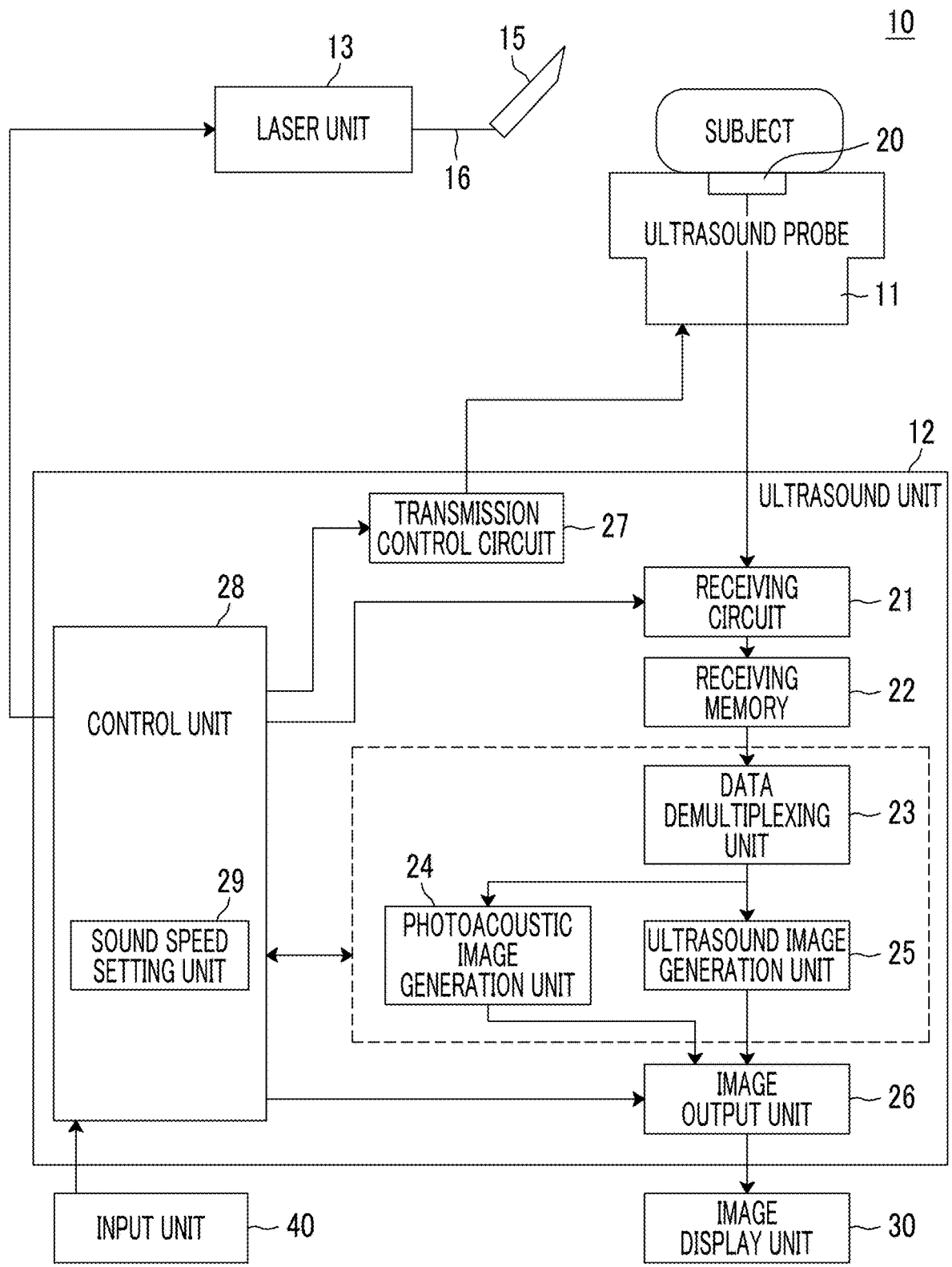
FIG. 1 is a block diagram illustrating the schematic configuration of a photoacoustic image generation apparatus which is an embodiment of an image generation apparatus of the invention.

Hereinafter, a photoacoustic image generation apparatus which is an embodiment of an image generation apparatus of the invention will be described in detail with reference to drawings. FIG. 1 is a block diagram illustrating the schematic configuration of the photoacoustic image generation apparatus.

As illustrated in FIG. 1, a photoacoustic image generation apparatus 10 according to the embodiment comprises an ultrasound probe 11 as an acoustic wave detection means, an ultrasound unit 12, a laser unit 13, and a puncture needle 15 as an insert. The puncture needle 15 and the laser unit 13 are connected by an optical cable 16 having an optical fiber. The puncture needle 15 can be attached to and detached from the optical cable 16 and is disposable. An ultrasonic wave is used as an acoustic wave in the embodiment, but the invention is not limited to the ultrasonic wave. An acoustic wave with an audible frequency may be used as long as an appropriate frequency is selected according to, for example, an inspection target or a measurement condition.

The laser unit 13 comprises a solid-state laser light source using, for example, yttrium aluminum garnet (YAG) and alexandrite. Laser light emitted from the solid-state laser light source of the laser unit 13 is guided by the optical cable 16 and is incident on the puncture needle 15. The laser unit 13 according to the embodiment emits pulsed laser light in a near-infrared wavelength range. The near-infrared wavelength range means a wavelength range of about 700 nm (nanometer) to 2500 nm (nanometer). The solid-state laser light source is used in the embodiment. However, another laser light source such as a gas laser light source may be used or a light source other than the laser light source may be used.

Figure 2:
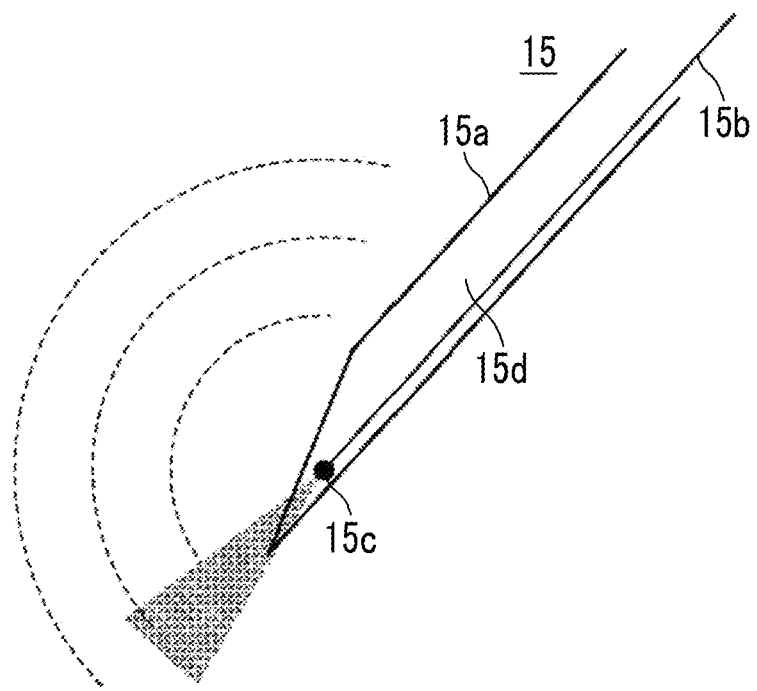
FIG. 2 is a cross-sectional view of the configuration of a tip portion of a puncture needle.

The puncture needle 15 is an embodiment of the insert according to the invention and is a needle that is inserted into a subject. FIG. 2 is a cross-sectional view including a center axis that extends in a length direction of the puncture needle 15. The puncture needle 15 includes a puncture needle main body 15a that has an opening at an acute tip and is formed in a hollow shape, an optical fiber 15b that guides laser light emitted from the laser unit 13 to the vicinity of the opening of the puncture needle 15, and a photoacoustic wave generation portion 15c that absorbs laser light emitted from the optical fiber 15b and generates a photoacoustic wave.

The optical fiber 15b and the photoacoustic wave generation portion 15c are disposed in a hollow portion 15d of the puncture needle main body 15a. For example, the optical fiber 15b is connected to the optical fiber in the optical cable 16 (refer to FIG. 1) through an optical connector that is provided at a base end of the puncture needle 15. For example, laser light of 0.2 mJ (millijoule) is emitted from a light emission end of the optical fiber 15b.

The photoacoustic wave generation portion 15c is provided at the light emission end of the optical fiber 15b and is provided near the tip of the puncture needle 15 and in the inner wall of the puncture needle main body 15a. The photoacoustic wave generation portion 15c absorbs the laser light emitted from the optical fiber 15b and generates photoacoustic waves. The photoacoustic wave generation portion 15c is made of, for example, an epoxy resin, a polyurethane resin, a fluorine resin, and silicone rubber with which a black pigment is mixed. The photoacoustic wave generation portion 15c is illustrated to be larger than the optical fiber 15b in FIG. 2, but the invention is not limited thereto. The photoacoustic wave generation portion 15c may have a size that is equal to a diameter of the optical fiber 15b.

The photoacoustic wave generation portion 15c is not limited to the above, and a metal film or an oxide film having light absorptivity with respect to the wavelength of laser light may be used as the photoacoustic wave generation portion. An oxide film made of, for example, iron oxide, chromium oxide, or manganese oxide having high light absorptivity with respect to the wavelength of laser light can be used as the photoacoustic wave generation portion 15c. Alternatively, a metal film made of, for example, titanium (Ti) or platinum (Pt) that has lower light absorptivity than an oxide but higher biocompatibility than an oxide may be used as the photoacoustic wave generation portion 15c. In addition, a position where the photoacoustic wave generation portion 15c is provided is not limited to the inner wall of the puncture needle main body 15a. For example, a metal film or an oxide film which is the photoacoustic wave generation portion 15c may be formed on the light emission end of the optical fiber 15b with a film thickness of about 100 nm (nanometer) by vapor deposition or the like such that the oxide film covers the light emission end. In this case, at least a part of the laser light emitted from the light emission end of the optical fiber 15b is absorbed by the metal film or the oxide film covering the light emission end and the photoacoustic wave is generated from the metal film or the oxide film.

Returning to FIG. 1, the ultrasound probe 11 detects the photoacoustic wave emitted from the photoacoustic wave generation portion 15c after the puncture needle 15 is inserted into the subject. The ultrasound probe 11 comprises an acoustic wave detection unit 20 that detects the photoacoustic waves.

The acoustic wave detection unit 20 comprises a piezoelectric element array in which a plurality of piezoelectric elements, that detects the photoacoustic waves, are one-dimensionally arranged and a multiplexer. The piezoelectric element is an ultrasound transducer, and the ultrasound transducer is a piezoelectric element made of a polymer film such as piezoelectric ceramics or polyvinylidene fluoride (PVDF). The acoustic wave detection unit 20 comprises an acoustic lens, an acoustic matching layer, a backing member, a control circuit of the piezoelectric element array, and the like (not illustrated).

With the piezoelectric element array of the acoustic wave detection unit 20, the ultrasound probe 11 transmits the acoustic wave (ultrasonic wave) to the subject and receives the reflected acoustic wave (reflected ultrasonic wave) with respect to the transmitted ultrasonic wave, in addition to the detection of the photoacoustic wave. The transmission and reception of the ultrasonic wave may be performed at separated positions. For example, the ultrasonic wave may be transmitted from a position different from the ultrasound probe 11, and the piezoelectric element array of the ultrasound probe 11 may receive the reflected ultrasonic wave with respect to the transmitted ultrasonic wave. It is possible to use a linear ultrasound probe, a convex ultrasound probe, a sector ultrasound probe, or the like as the ultrasound probe 11.

The ultrasound unit 12 has a receiving circuit 21, a receiving memory 22, a data demultiplexing unit 23, a photoacoustic image generation unit 24, an ultrasound image generation unit 25, an image output unit 26, a transmission control circuit 27, and the control unit 28. The control unit 28 comprises a function as a sound speed setting unit 29 that sets the sound speed in the subject. The ultrasound unit 12 typically has, for example, a processor, a memory, and a bus. In the ultrasound unit 12, a program relating to a photoacoustic image generation processing, an ultrasound image generation processing, a sound speed setting processing, and the like is incorporated in a memory. The program is operated by the control unit 28 which is formed by the processor to realize functions of the data demultiplexing unit 23, the photoacoustic image generation unit 24, the ultrasound image generation unit 25, the sound speed setting unit 29, and the like. That is, each of these units is formed by the memory into which the program is incorporated and the processor.

The hardware configuration of the ultrasound unit 12 is not particularly limited and can be realized by combining a plurality of integrated circuits (ICs), a processor, an application specific integrated circuit (ASIC), a field-programmable gate array (FPGA), a memory, and the like as appropriate.

The receiving circuit 21 receives a detection signal output from the ultrasound probe 11 and stores the received detection signal in the receiving memory 22. The receiving circuit 21 typically includes a low-noise amplifier, a variable-gain amplifier, a low pass filter, and an analog to digital converter (AD). The detection signal of the ultrasound probe 11 is amplified by the low-noise amplifier, is subjected to gain adjustment corresponding to a depth by the variable-gain amplifier, is converted into a digital signal by the AD converter after high-frequency components of the detection signal is cut by the low pass filter, and then is stored in the receiving memory 22. The receiving circuit 21 is formed by, for example, one IC.

The ultrasound probe 11 outputs a detection signal of the photoacoustic wave and a detection signal of the reflected ultrasonic wave. The receiving memory 22 stores the AD-converted detection signals (sampling data) of the photoacoustic wave and the reflected ultrasonic wave. The data demultiplexing unit 23 reads out the detection signal of the photoacoustic wave from the receiving memory 22 and transmits the detection signal to the photoacoustic image generation unit 24. The data demultiplexing unit 23 reads out the detection signal of the reflected ultrasonic wave from the receiving memory 22 and transmits the detection signal to the ultrasound image generation unit 25.

The photoacoustic image generation unit 24 generates a photoacoustic image based on the detection signal of the photoacoustic wave detected by the ultrasound probe 11. The photoacoustic image generation processing includes, for example, image reconfiguration such as phase matching addition, detection, and logarithmic conversion. The ultrasound image generation unit 25 generates an ultrasound image based on the detection signal of the reflected ultrasonic wave detected by the ultrasound probe 11. The ultrasound image generation processing also includes image reconfiguration such as phase matching addition, detection, logarithmic conversion, and the like. The image output unit 26 outputs the photoacoustic image, the ultrasound image, and the like on an image display unit 30 such as a display apparatus.

The control unit 28 controls each unit in the ultrasound unit 12. In a case where a photoacoustic image is acquired, the control unit 28 transmits a trigger signal to the laser unit 13 to cause the laser unit 13 to emit laser light. In addition, the control unit 28 transmits a sampling trigger signal to the receiving circuit 21 to control a sampling start timing of the photoacoustic wave or the like with the emission of the laser light. The sampling data received by the receiving circuit 21 is stored in the receiving memory 22.

The photoacoustic image generation unit 24 receives the sampling data of the detection signal of the photoacoustic wave through the data demultiplexing unit 23 and performs detection at a predetermined detection frequency to generate the photoacoustic image. The photoacoustic image generated by the photoacoustic image generation unit 24 is input to the image output unit 26.

In a case where a ultrasound image is acquired, the control unit 28 transmits an ultrasound transmission trigger signal for instructing the transmission control circuit 27 to transmit the ultrasonic wave. In a case where the ultrasound transmission trigger signal is received, the transmission control circuit 27 causes the ultrasound probe 11 to transmit the ultrasonic wave. In a case where the ultrasound image is acquired, the ultrasound probe 11 performs a scanning, for example, while shifting a reception region of a group of piezoelectric elements line by line to detect the reflected ultrasonic wave by the control of the control unit 28. The control unit 28 transmits the sampling trigger signal to the receiving circuit 21 according to a transmission timing of the ultrasonic wave to start the sampling of the reflected ultrasonic wave. The sampling data received by the receiving circuit 21 is stored in the receiving memory 22.

The ultrasound image generation unit 25 receives the sampling data of the detection signal of the ultrasonic wave through the data demultiplexing unit 23 and performs the detection at a predetermined detection frequency to generate the ultrasound image. The ultrasound image generated by the ultrasound image generation unit 25 is input to the image output unit 26.

The image output unit 26 synthesizes the photoacoustic image generated by the photoacoustic image generation unit 24 and the ultrasound image generated by the ultrasound image generation unit 25 to generate a display image and outputs the generated display image on the image display unit 30 such as a display apparatus. The image output unit 26 can individually output and display the photoacoustic image and the ultrasound image on the image display unit 30 without synthesizing both images.

Figure 3:
FIG. 3 is a view of an example of an image in which an ultrasound image and a photoacoustic image are superimposed.
Figure 4:
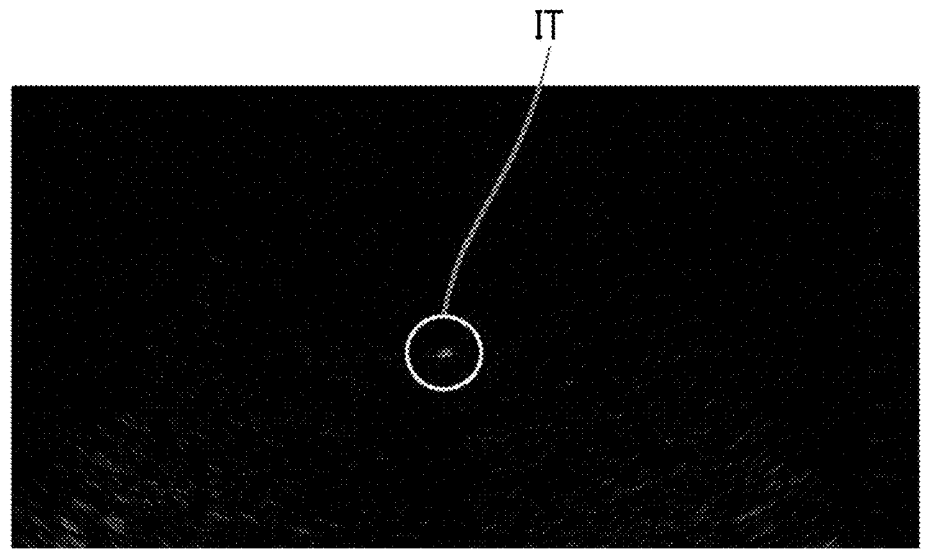
FIG. 4 is a view of only the photoacoustic image in the superimposed image illustrated in FIG. 3.

Here, a method of correcting the sound speed of the photoacoustic image in the photoacoustic image generation apparatus 10 according to the embodiment will be described in detail. FIG. 3 is a view of an example of an image in which an ultrasound image and a photoacoustic image are superimposed, and FIG. 4 is a view of only the photoacoustic image in the superimposed image illustrated in FIG. 3.

As illustrated in FIG. 3, the photoacoustic image generation apparatus 10 can display the image in which the ultrasound image and the photoacoustic image are superimposed. The ultrasound image and the photoacoustic image are generated based on a detection signal output from the ultrasound probe 11 and a sound speed set in advance (for example, an average sound speed in the subject). In addition, since the photoacoustic wave generation portion 15c is provided at the tip portion of the puncture needle 15, the tip portion of the puncture needle 15 can be selectively imaged in the photoacoustic image as illustrated in FIG. 4. In the photoacoustic image, it is necessary to accurately check a tip position of the puncture needle 15 in the subject. Therefore, an image with particularly high resolution is required.

It is conceivable to perform the sound speed correction processing on the photoacoustic image. However, the load is extremely large in the case where the sound speed correction processing is performed on the entire photoacoustic image. Therefore, it is possible to reduce the load for the sound speed correction processing by specifying a region having a predetermined range including the tip portion of the puncture needle 15 (hereinafter referred to as a tip region) in the photoacoustic image and performing the sound speed correction processing only on the tip region.

However, in a case where a region having a predetermined range including a pixel having the highest brightness or contrast in an image is set as an interested region and the sound speed correction processing is performed only on the interested region as in JP2014-147825A, there is a possibility that the tip region of the puncture needle 15 is out of the sound speed correction range and thus the resolution of the tip region of the puncture needle 15 is reduced in a case where a pixel of a noise portion has higher brightness or contrast than a pixel indicating the tip portion of the puncture needle 15.

Figure 5:
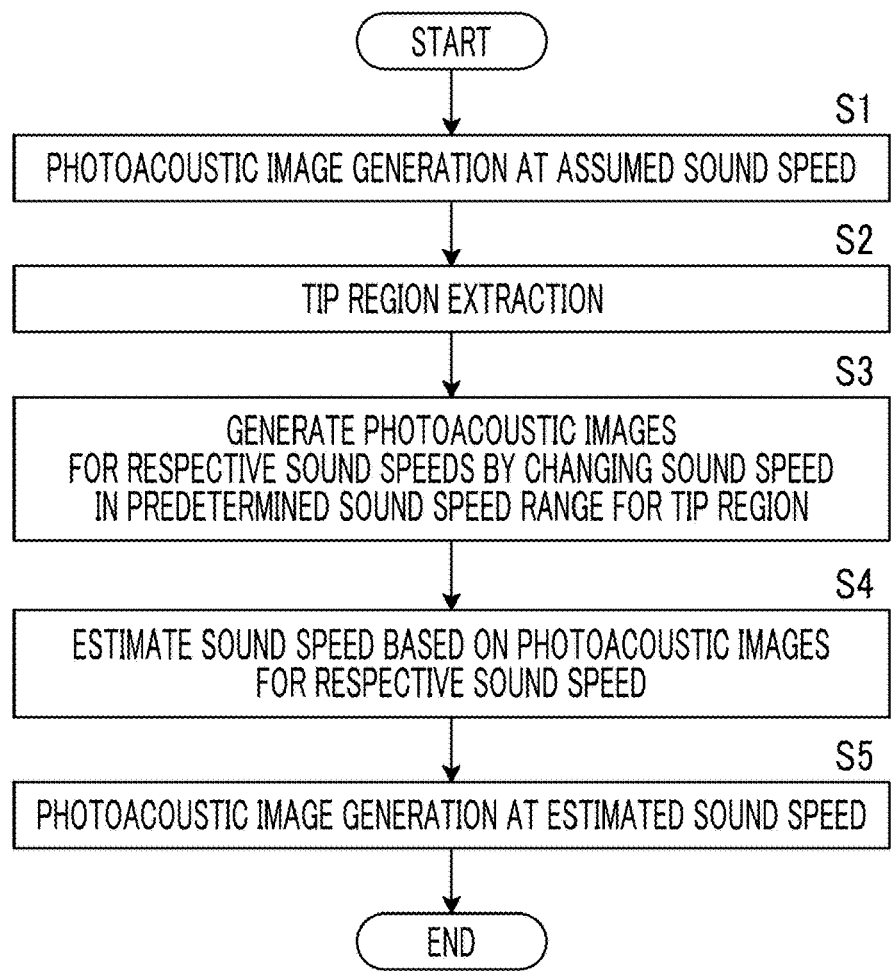
FIG. 5 is a flowchart for describing a method of sound speed correction processing of a photoacoustic image.

For this reason, the region having the predetermined range (tip region) including the tip portion of the puncture needle 15 is accurately extracted from the photoacoustic image, and the sound speed correction processing is reliably performed on the tip region in the embodiment. FIG. 5 is a flowchart for describing the method of the sound speed correction processing of the photoacoustic image in the photoacoustic image generation apparatus 10 according to the embodiment.

As illustrated in FIG. 5, first, a photoacoustic image is generated based on an assumed sound speed and a detection signal acquired by the ultrasound probe 11 (step S1). Any speed of, for example, 1530 m/s (meter/second) or 1540 m/s (meter/second) which is an average sound speed in the subject may be set as the assumed sound speed. In the embodiment, "assumed sound speed" refers to any sound speed in a sound speed range conceivable as the "sound speed in the subject".

Next, a region having a predetermined range including a high signal value pixel collection portion having a region size larger than a reference region size is extracted as the tip region in the photoacoustic image generated based on the assumed sound speed (step S2).

Here, the "high signal value pixel collection portion" means a collection portion of pixels representing a region where a signal value of the detection signal acquired by the ultrasound probe 11 is high, and means a collection portion of a group of pixels having a signal value equal to or larger than a predetermined threshold value such as the pixel indicating the tip portion of the puncture needle 15 or the pixel indicating the noise. That is, in the case of an image that is displayed with higher brightness as the signal value is higher, the high signal value pixel collection portion becomes a collection portion of high brightness pixels as illustrated in FIG. 4. On the contrary, in the case of an image that is displayed with higher brightness as the signal value is lower, the high signal value pixel collection portion becomes a collection portion of low brightness pixels.

In the photoacoustic image illustrated in FIG. 4, a high brightness pixel collection portion indicated by IT indicates the tip portion of the puncture needle 15, and high brightness pixel collection portions other than the high brightness pixel collection portion are simply noise. A time for noise to appear on the photoacoustic image is often short. In addition, sound ray data (raw data) acquired by the ultrasound probe 11 generally has a lower information density in a lateral direction (azimuth direction) than a vertical direction (depth direction). In a case where the sound ray data is displayed as the ultrasound image, interpolation processing is usually performed on image information in the lateral direction. For this reason, one point of noise is spread and displayed in the lateral direction on the sound ray data. As a result, the tip portion of the puncture needle 15 has a certain length in both directions of the depth direction (vertical direction in FIG. 6) and the lateral direction as illustrated in an enlarged view of FIG. 6. On the other hand, the noise has a length in the lateral direction, but is not so long in the depth direction (vertical direction in FIG. 7) as illustrated in an enlarged view of FIG. 7.

As described above, the size of the high signal value pixel collection portion indicating the tip portion of the puncture needle 15 tends to be larger than the size of the high signal value pixel collection portion indicating the noise. Therefore, the region having the predetermined range including the high signal value pixel collection portion having the region size larger than the reference region size is extracted as the tip region in step S2.

The reference region size in step S2 may be set in both directions of the depth direction (vertical direction) and the lateral direction or may be set only in the depth direction (vertical direction). As described above, there is a state in which the tip portion of the puncture needle 15 has a certain length in both directions of the depth direction and the lateral direction, whereas the noise has a length in the lateral direction but is not so long in the depth direction. For this reason, it is possible to identify the tip portion of the puncture needle 15 and the noise only by the size in the depth direction. However, the sound ray data having a certain length also in the lateral direction by comparing also the size in the lateral direction may be specified as the tip portion of the puncture needle 15 in order to ensure more accuracy.

The reference region size may be adjusted based on a type of needle which is the insert, a generation condition of the photoacoustic wave, a type of acoustic wave detection means, frequency characteristics of the acoustic wave detection means, a reception detection frequency band for the acoustic wave detection means, or a display size of the photoacoustic image. For example, an initial value may be set for the reference region size, and the reference region size may be adjusted based on each item condition.

First, a case where the reference region size is adjusted based on the type of needle which is the insert will be described. In general, the photoacoustic wave generation portion becomes larger and a reflection distance from the needle also becomes larger as a diameter of the needle becomes larger. Therefore, a reception signal from a needle tip increases. Accordingly, the reference region size may be larger as the needle diameter becomes larger. Even in a case where the needle diameter is the same, the larger the photoacoustic wave generation portion, the larger the reception signal from the needle tip. Accordingly, the reference region size may be larger as the photoacoustic wave generation portion becomes larger. As described above, the magnitude of the reception signal from the needle tip changes according to the type of needle (differences in the needle diameter and/or the size of the photoacoustic wave generation portion). Therefore, it is possible to set an optimum reference region size according to the type of needle by setting the type of the needle through the input unit 40. An identification unit for identifying the type of the needle may be provided in a part of the needle to automatically identify the type of the needle in the apparatus.

Next, a case where the reference region size is adjusted based on the generation condition of the photoacoustic wave will be described. For example, the generation condition thereof is a drive condition of the laser unit 13 that generates laser light to be irradiated to the photoacoustic wave generation portion 15c, and the reception signal from the needle tip becomes larger as the number of pulses of the laser light to be irradiated to the photoacoustic wave generation portion 15c becomes larger. Accordingly, the reference region size may be larger as the number of pulses of the laser light to be irradiated to the photoacoustic wave generation portion 15c becomes larger. For example, in a case where the number of pulses is changed from 1 to 3, the reference region size may be set to three times in a transmission and reception direction (vertical direction in the image) of the ultrasonic wave.

Next, a case where the reference region size is adjusted based on the type of the acoustic wave detection means will be described. In a case where the frequency characteristics of the acoustic wave detection means are the same, a linear type has a high resolution and the reception signal from the needle becomes small. Therefore, the reference region size may be reduced. Since a sector type and a convex type have low resolution and the reception signal from the needle is large, the reference region size may be increased.

Next, a case where the reference region size is adjusted based on the frequency characteristics of the acoustic wave detection means will be described. In a case where the frequency characteristic of the acoustic wave detection means is low, the reception signal from the needle becomes large. Therefore, the reference region size may be larger as the frequency characteristic of the acoustic wave detection means becomes lower.

Next, a case where the reference region size is adjusted based on the reception detection frequency band for the acoustic wave detection means will be described. In a case where the reception detection frequency band (for example, center frequency) for the acoustic wave detection means is low, the reception signal from the needle becomes large. Therefore, the reference region size may be larger as the reception detection frequency band for the acoustic wave detection means is lower.

Next, a case where the reference region size is adjusted based on the display size of the photoacoustic image will be described. In a case where a needle region is enlarged by zooming or the like, the display size of the needle region increases. Therefore, the reference region size may be larger as the needle region is displayed in a larger manner.

A reference region size management table in which each item condition and the reference region size are recorded in association with each other may be stored in advance in a memory (not illustrated) and a matching reference region size in the reference region size management table may be extracted and set according to each item condition, in addition to the aspect in which the initial value is set for the reference region size and the reference region size is adjusted based on each item condition.

For example, a reference region size management table in which each item condition, of the type of acoustic wave detection means (linear type/convex type), the type of needle (thickness 22 gauge/27 gauge), the generation condition of the photoacoustic wave (2 pulses/4 pulses), and the reception detection center frequency (2 MHz (megahertz)/4 MHz (megahertz)/8 MHz (megahertz)), and the reference region size (only in the depth direction of the photoacoustic image) are recorded in association with each other may be stored in advance in a memory (not illustrated) and a matching reference region size in the reference region size management table may be extracted and set according to each item condition.

As an example of the numerical values in this case, in a case where a linear type probe is used, the needle thickness is 22 gauge, the number of photoacoustic wave pulses is two, and the reception detection center frequency is 8 MHz (megahertz), the reference region size may be set to 0.13 mm (millimeter). In a case where a linear type probe is used, the needle thickness is 22 gauge, the number of photoacoustic wave pulses is two, and the reception detection center frequency is 4 MHz (megahertz), the reference region size may be set to 1.09 mm (millimeter). In addition, in a case where a convex type probe is used, the needle thickness is 22 gauge, the number of photoacoustic wave pulses is two, and the reception detection center frequency is 4 MHz (megahertz), the reference region size may be set to 0.25 mm (millimeter). In a case where a convex type probe is used, the needle thickness is 22 gauge, the number of photoacoustic wave pulses is two, and the reception detection center frequency is 2 MHz (megahertz), the reference region size may be set to 2.19 mm (millimeter).

In addition, in a case where a reference region size that completely matches each item condition cannot be extracted after the reference region size management table is provided, a reference region size closest to each item condition may be extracted and items different from the reference region size management table may be finely adjusted for each item as described above with the reference region size as the initial value.

In step S2, the method of extracting the region having the predetermined range including the high signal value pixel collection portion having the region size larger than the reference region size as the tip region in the photoacoustic image generated based on the assumed sound speed is not particularly limited, and any method may be used.

For example, a high signal value pixel collection portion having the region size larger than the reference region size may be specified by image recognition, and a region having a predetermined range including the extracted high signal value pixel collection portion may be extracted to set as the tip region.

In addition, reduction processing of reducing signal intensity of the high signal value pixel collection portion having a region size smaller than the reference region size may be performed on the photoacoustic image generated based on the assumed sound speed and the detection signal, and a region having a predetermined range including a pixel having the highest signal value may be extracted as the tip region in the photoacoustic image subjected to the reduction processing.

Here, the reduction processing may be a low pass filter processing having a half-width of 0.5 times or more to 2 times or less the reference region size, or may be a smoothing filter processing.

It is possible to use moving average filter processing, Gaussian filter processing, or the like as the smoothing filter processing.

As described above, since the time for noise to appear on the photoacoustic image is often short on the photoacoustic image, there is a tendency that the tip portion of the puncture needle 15 has a certain length in the depth direction, whereas the noise has a length in the lateral direction but is not so long in the depth direction. Therefore, the smoothing filter processing can prevent the resolution in the lateral direction from being reduced while reducing the signal intensity of the noise portion by increasing a smoothing effect in the depth direction in the photoacoustic image more than a smoothing effect in the lateral direction therein.

Figure 6:
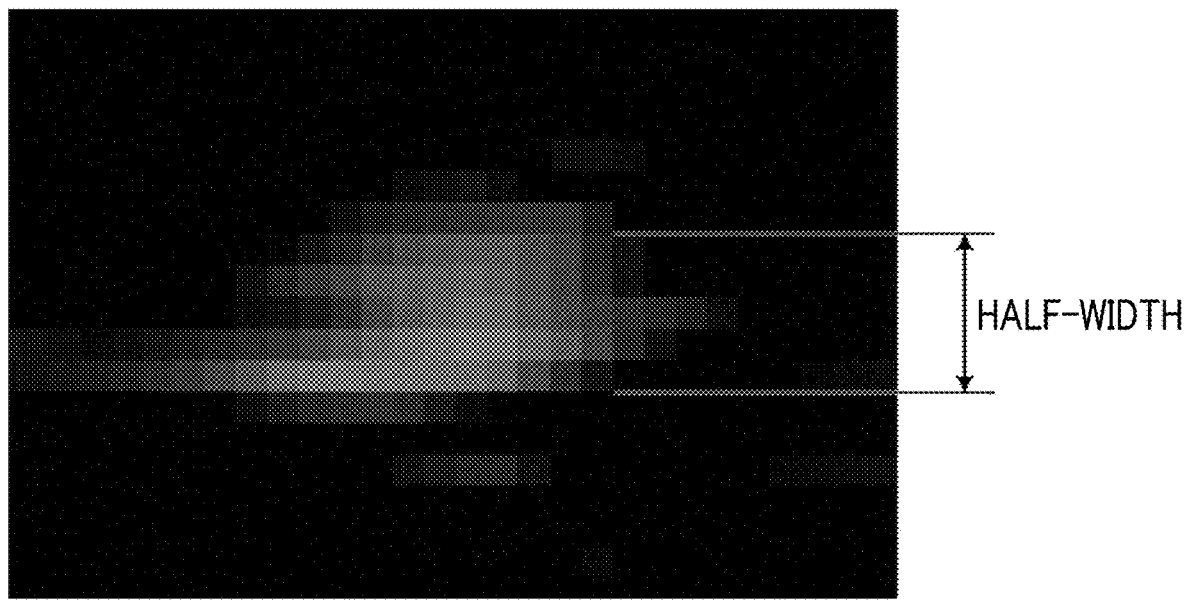
FIG. 6 is an enlarged view of the tip portion of the puncture needle in the photoacoustic image illustrated in FIG. 4.
Figure 7:
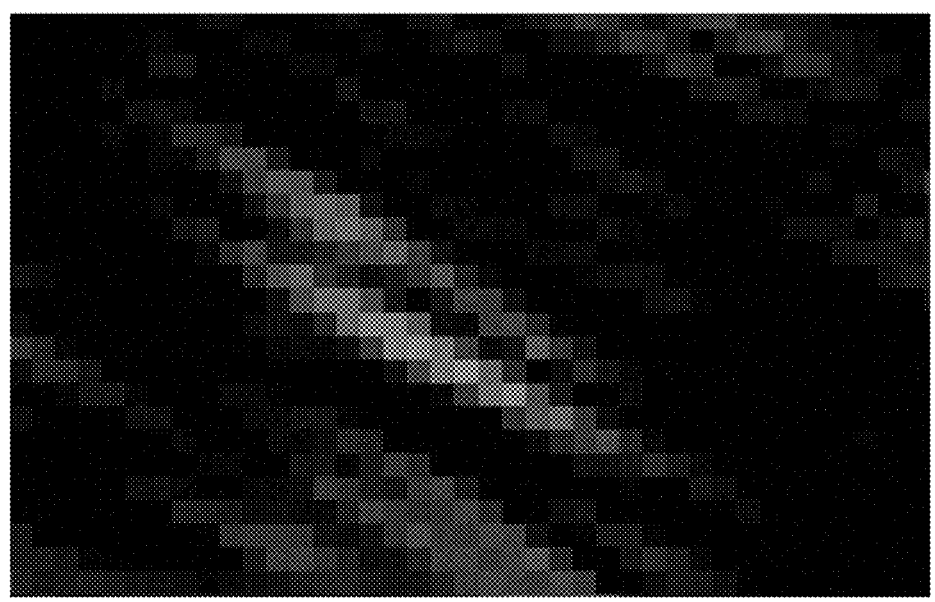
FIG. 7 is an enlarged view of a noise portion of the photoacoustic image illustrated in FIG. 4.

For example, in a case where the half-width of the signal intensity in the high signal value pixel collection portion indicating the tip portion of the puncture needle 15 is five pixels, a moving average filter of 5 rows of [1,1,1,1,1]/5 in the depth direction may be used as a simple example, as illustrated in FIG. 6. This is an extreme example, and a two-dimensional smoothing filter may be used in which the smoothing effect in the depth direction is larger than the smoothing effect in the lateral direction.

Figure 8:
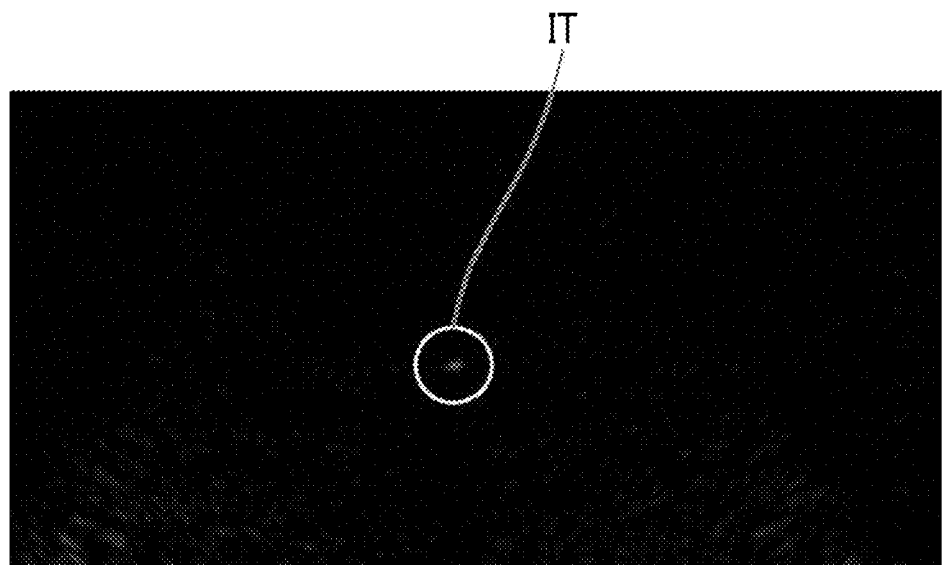
FIG. 8 is a view of a photoacoustic image after reduction processing.
Figure 9:
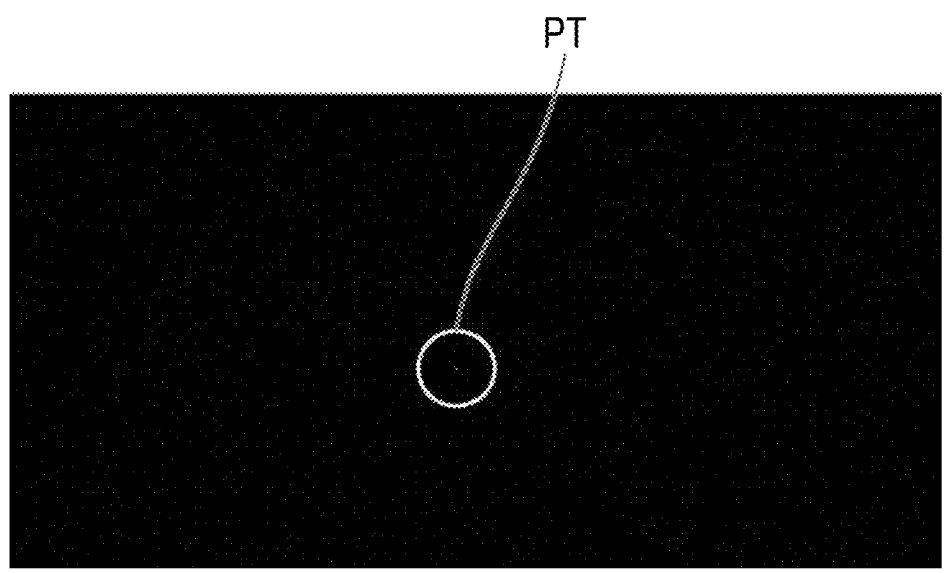
FIG. 9 is a view of a photoacoustic image after cut-off filter processing.

In a case where the above reduction processing is performed on the photoacoustic image illustrated in FIG. 4, it is possible to obtain an image in which the signal intensity of the noise portion is reduced while the signal intensity of the pixel collection portion IT indicating the tip portion of the puncture needle 15 is maintained as illustrated in FIG. 8. By performing the cut-off filter processing for reducing a signal value of a pixel having a predetermined signal intensity or less to zero on this image, it is possible to obtain an image in which only a part of the pixels at the tip portion of the puncture needle 15 remains as a bright point PT and all noise portions disappear as illustrated in FIG. 9. By extracting a region having a predetermined range including the pixel having the highest signal value as the tip region in this image, it is possible to accurately extract the region of the tip portion of the puncture needle 15 as the tip region.

In a case where parameters in the reduction processing are not appropriate, it is impossible to completely erase the noise portion and accurately extract the region of the tip portion of the puncture needle 15 as the tip region. Therefore, the parameters in the reduction processing may be appropriately adjusted manually or automatically based on the type of the needle which is the insert, the generation condition of the photoacoustic wave, the type of the acoustic wave detection means, the frequency characteristics of the acoustic wave detection means, and the reception detection frequency band for the acoustic wave detection means, or the display size of the photoacoustic image, similar to the above adjustment of the reference region size.

Next, the sound speed is changed in a predetermined sound speed range with respect to the tip region to generate a photoacoustic image for each sound speed (step S3). The predetermined sound speed range may be set to a range conceivable as the sound speed in the subject, for example, a range of 1350 m/s (meter/second) to 1550 m/s (meter/second), preferably 1350 m/s (meter/second) to 1650 m/s (meter/second) and can be set according to a site to be imaged as appropriate.

Next, a sound speed of a photoacoustic image having the maximum image evaluation value is estimated as the actual sound speed in the subject among the photoacoustic images generated for respective sound speeds, and this sound speed is set as the sound speed in the subject (Step S4).

Here, the image evaluation value may be an evaluation value indicating a smallness of intensity variation of a signal phase-adjusted based on the sharpness of the photoacoustic image, the contrast of the photoacoustic image, the sound speed at the time of image generation in the tip region, or the like. However, the invention is not limited to the above, but any evaluation value may be used as long as the evaluation value indicates the image quality of the photoacoustic image. This image evaluation value may be calculated based on pixel arrangements in both directions of the photoacoustic image in the lateral direction and the depth direction (vertical direction), may be calculated based on the pixel arrangement only in the lateral direction thereof, or may be calculated based on the pixel arrangement only in the depth direction (vertical direction) thereof. The sound speed correction in the image generation apparatus according to the embodiment of the invention is effective in improving the image quality particularly in the lateral direction of the lateral direction and depth direction (vertical direction) of the photoacoustic image. Therefore, it is preferable to calculate the image evaluation value of the photoacoustic image based on the pixel arrangement only in the lateral direction. In this manner, it is possible to suppress an amount of calculation in a case where the image evaluation value is calculated by calculating the image evaluation value of the photoacoustic image based on the pixel arrangement only in one direction.

For the method of calculating the image evaluation value of the photoacoustic image based on the pixel arrangement only in one direction of the lateral direction and the depth direction (vertical direction), in a case where the image evaluation value thereof is calculated based on the pixel arrangement only in the lateral direction, the image evaluation value may be calculated for each pixel in one lateral row of the photoacoustic image to be evaluated and a value obtained by adding all the two-dimensional regions of the photoacoustic image to be evaluated may be used as the image evaluation value. Alternatively, the image evaluation value may be a value obtained by averaging the value obtained by adding all the two-dimensional regions of the photoacoustic image to be evaluated with the number of pixels in the vertical direction. In the case where only the vertical direction is considered, the image evaluation value may be calculated for each pixel in one vertical column and a total value or an average value of the entire two-dimensional region of the photoacoustic image may be used as the image evaluation value in the same manner as described above. The calculation method of the evaluation value is not limited to the above, and any method may be used for the calculation.

Figure 10:
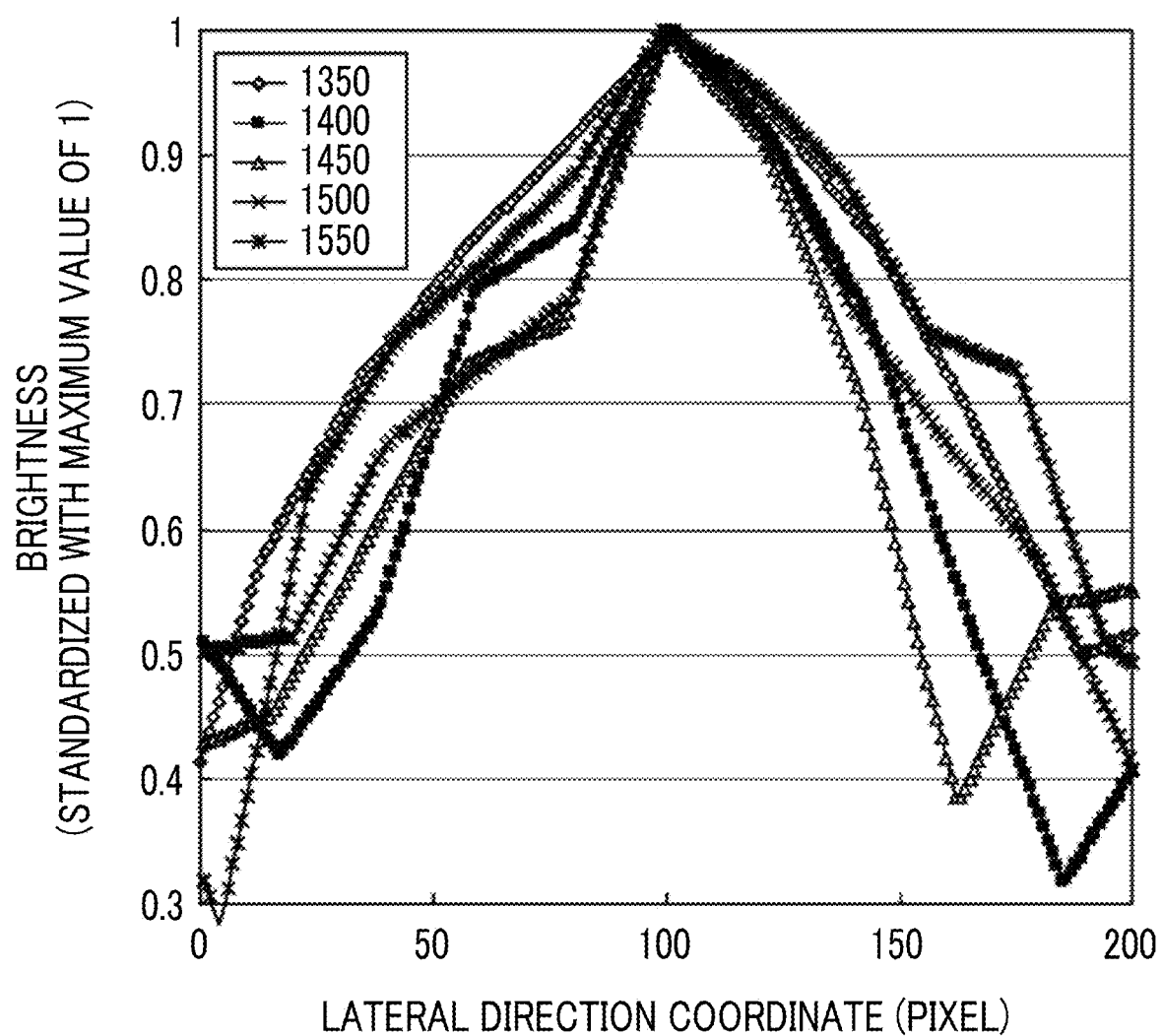
FIG. 10 is a graph illustrating image profiles in a lateral direction in a case where the sound speed is changed in a predetermined sound speed range to generate photoacoustic images.
Figure 11:
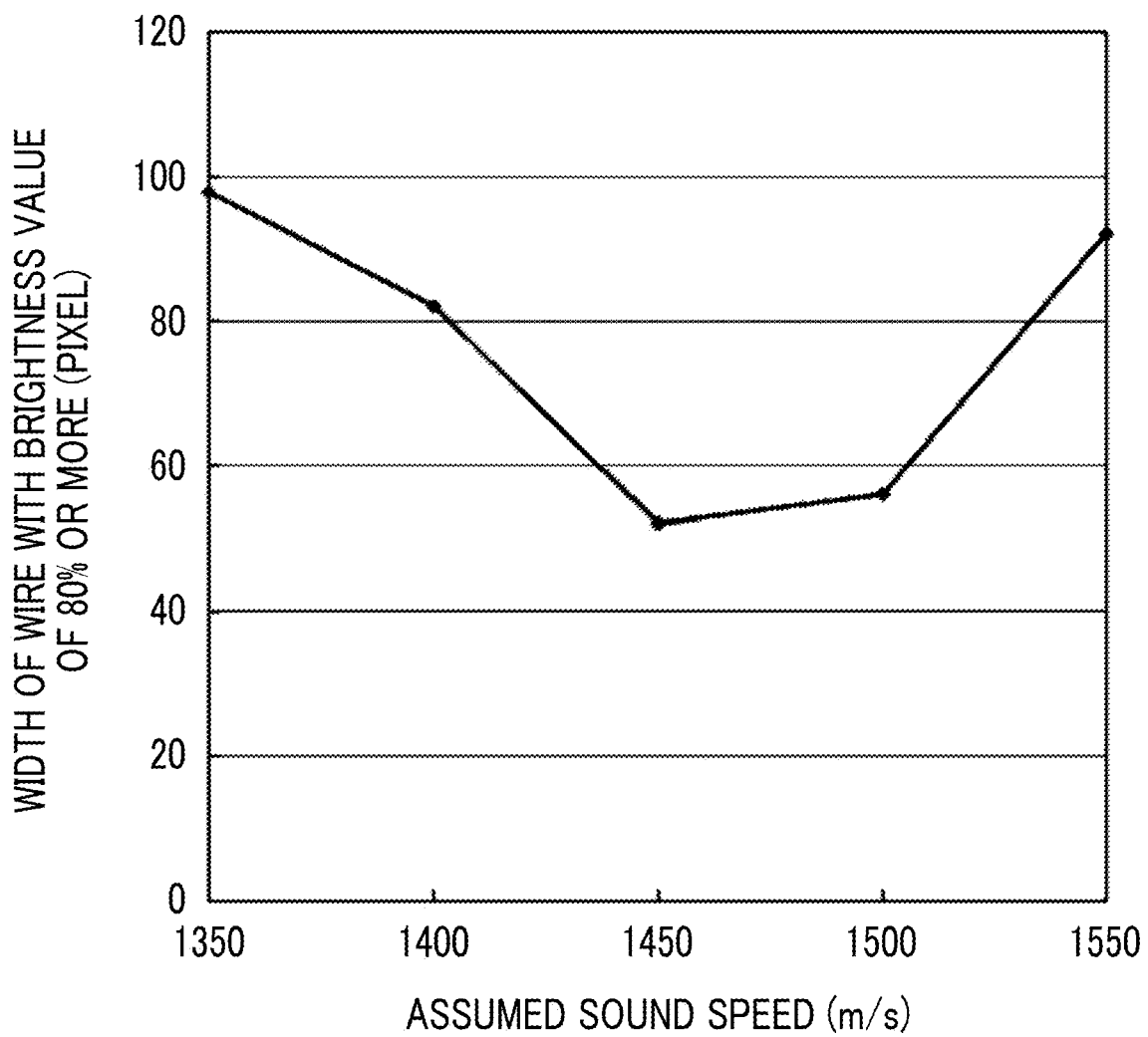
FIG. 11 is a graph illustrating sharpness of the photoacoustic images generated for respective sound speeds.

The processing of step S4 will be described in detail with an example. FIG. 10 is a graph illustrating image profiles in the lateral direction in a case where the predetermined sound speed has a range from 1350 m/s (meter/second) to 1550 m/s (meter/second) and a photoacoustic image is generated every 50 m/s (meter/second). FIG. 11 is a graph illustrating the sharpness (image evaluation value) of the photoacoustic images generated for respective sound speeds. In the graph of FIG. 11, the vertical axis indicates a width of the tip portion of the puncture needle 15 in the photoacoustic image, and the sharpness becomes higher as the numerical value on the vertical axis becomes lower.

In the examples illustrated in FIGS. 10 and 11, the sharpness (image evaluation value) of the photoacoustic image generated at the sound speed of 1450 m/s (meter/second) is the maximum. Therefore, 1450 m/s (meter/second) is set as the sound speed in the subject.

The calculation load is remarkably reduced as described below in a case where the processing in steps S3 and S4 is performed only on the tip region as compared with the case where the processing is performed on the entire region of the photoacoustic image. Therefore, it is also possible to perform the processing in real-time.

For example, the display region size of 0.1 cm$^2$ (square centimeter) (0.3 cm (centimeter)×0.3 cm (centimeter)) for the tip region of the puncture needle 15 is sufficient in a case where the display region size of the entire image is 100 cm$^2$ (square centimeter) (10 cm (centimeter)×10 cm (centimeter)), and an area ratio thereof is 1000:1. For this reason, in a case where the above processing is performed only on the tip region, the calculation load can be reduced to $\frac{1}{1000}$.

Finally, a photoacoustic image is generated at the sound speed set in step S4 (step S5), and the photoacoustic image generation processing ends.

Figure 12:
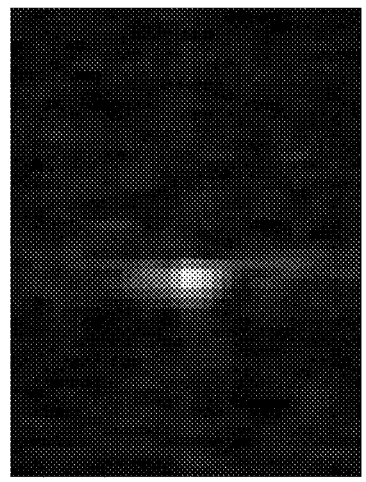
FIG. 12 is a view of an example of an image generated at an appropriate sound speed.
Figure 13:
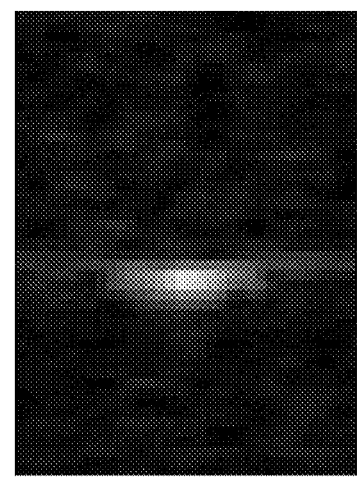
FIG. 13 is a view of an example of an image generated at an inappropriate sound speed.

For example, the sharpness (image evaluation value) of the photoacoustic image generated at the sound speed of 1450 m/s (meter/second) is the maximum in the examples illustrated in FIGS. 10 and 11, and an example of an image generated with the sound speed in the subject as 1450 m/s (meter/second) is illustrated in FIG. 12. On the contrary, FIG. 13 illustrates an example of an image generated at 1540 m/s (meter/second) which is substantially equivalent to the assumed sound speed in step S1. It can be seen that the image illustrated in FIG. 12 has a higher resolution at the tip portion of the puncture needle 15 than the image illustrated in FIG. 13.

Figure 14:
FIG. 14 is a view of an example of a sound ray data image.

In the description of the above embodiment, for the photoacoustic image to be subjected to the sound speed correction processing, the sound speed correction processing is performed on the final image in which various kinds of image processing such as image deformation processing are performed on a sound ray data image obtained by beam-forming the detection signal acquired by the ultrasound probe 11 at a predetermined sound speed. However, the sound speed correction processing may be performed directly on the sound ray data image as illustrated in FIG. 14. The lateral direction of the sound ray data image of FIG. 14 corresponds to a sound ray, which is 0.16 mm/line (millimeter/sound ray), and the vertical direction (corresponding to the depth direction) thereof corresponds to a sample point of the sound ray data, which is 0.091 mm/sample (millimeter/sample). The detection signal is logarithmically compressed and the frame is mapped with 255 gradations to obtain brightness data. It is possible to obtain the same effect as described above even in a case where the sound speed correction processing is performed on such a sound ray data image.

Here, a simulation result of examining a parameter in the above reduction processing using the sound ray data image is illustrated.

Condition 1: In a case where the reception detection frequency for the acoustic wave detection means is 8 MHz (megahertz) and the number of light emissions is 2 (the number of pulses of laser light is 2), the half-width of the signal intensity at the tip portion of the puncture needle 15 is 0.91 mm (millimeter), which is about 4.7 times the wavelength of 0.193 mm at 8 MHz (megahertz). This is considered to be the influence of two light emissions and multiple reflection or the like at the needle tip.

Condition 2: In a case where the reception detection frequency for the acoustic wave detection means is 4 MHz (megahertz) and the number of light emissions is 2 (the number of pulses of laser light is 2), the half-width of the signal intensity at the tip portion of the puncture needle 15 is 1.64 mm (millimeter), which is about 4.2 times the wavelength of 0.386 mm at 4 MHz (megahertz). This is considered to be the influence of two light emissions and multiple reflection or the like at the needle tip. As compared with the half-width of Condition 1, the half-width of Condition 2 is approximately the same ratio as the ratio of both wavelengths.

Condition 3: In a case where the reception detection frequency for the acoustic wave detection means is 8 MHz (megahertz) and the number of light emissions is 4 (the number of pulses of laser light is 4), the half-width of the signal intensity at the tip portion of the puncture needle 15 is 1.46 mm (millimeter), which is about 7.6 times the wavelength of 0.193 mm at 8 MHz (megahertz). This is considered to be the influence of four light emissions and multiple reflection or the like at the needle tip. As compared with the half-width of Condition 1, the half-width of Condition 3 is approximately the same ratio as the ratio of the number of light emissions in both conditions.

As described above, it has been found that the half-width is approximately proportional to the wavelength of the reception frequency and the number of light emissions. The filter in the reduction processing is designed such that a signal having a size equal to or less than the half-width is reduced and a signal having a size equal to or larger than the half-width is left.

As a result of the simulation, for Condition 2, with a moving average filter (18 rows) having 18 sample points in the depth direction corresponding to the half-width of 1.64 mm (millimeter), it is possible to reduce only the noise portion even in an image in which the signal intensity of the noise portion is higher than the signal intensity of the tip portion of the puncture needle 15 and to extract only the signal of the tip portion of the puncture needle 15 even in a case where a 70% relatively light cut-off filter is used.

For Condition 3, with a moving average filter (16 rows) having 16 sample points in the depth direction corresponding to the half-width of 1.46 mm (millimeter), it is possible to reduce only the noise portion even in an image in which the signal intensity of the noise portion is higher than the signal intensity of the tip portion of the puncture needle 15 and to extract only the signal of the tip portion of the puncture needle 15 even in a case where a 70% relatively light cut-off filter is used.

In the above embodiments, the puncture needle 15 is used as an embodiment of the insert. However, the insert is not limited thereto. The insert may be a radio-frequency ablation needle including an electrode that is used for radio-frequency ablation therein, a catheter that is inserted into a blood vessel, or a guide wire for a catheter that is inserted into a blood vessel. Alternatively, the insert may be an optical fiber for laser treatment.

The insert is not limited to a needle, such as an injection needle, and may be a biopsy needle used for biopsy. That is, the needle may be a biopsy needle that is inserted into an inspection target of the living body and extracts the tissues of a biopsy site of the inspection target. In this case, a photoacoustic wave may be generated from an extraction portion (intake port) for sucking and extracting the tissues of the biopsy site. In addition, the needle may be used as a guiding needle that is used for insertion into a deep portion, such as a portion under the skin or an organ inside the abdomen.

The invention has been described above based on the preferred embodiments. However, the image generation apparatus according to the embodiment of the invention is not limited only to the above embodiments. Various modifications and changes of the configurations according to the above embodiments are also included in the scope of the invention.

From the above description, it is possible to grasp the image generation apparatus described in the following additional item 1.

Additional Item 1

An image generation apparatus comprising:

a photoacoustic image generation processor that generates a photoacoustic image based on a detection signal acquired by detecting a photoacoustic wave emitted from a tip portion of an insert inserted into a subject using an acoustic wave detection means and a sound speed in the subject; and a sound speed setting processor that extracts a region having a predetermined range including a high signal value pixel collection portion having a region size larger than a reference region size as a tip region in a photoacoustic image generated based on an assumed sound speed and the detection signal, and sets a sound speed of a photoacoustic image having a maximum image evaluation value as the sound speed in the subject among photoacoustic images for respective sound speeds generated by changing the sound speed in a predetermined sound speed range for the tip region.

EXPLANATION OF REFERENCES

10: photoacoustic image generation apparatus
11: ultrasound probe
12: ultrasound unit
13: laser unit
15: puncture needle
15a: puncture needle main body
15b: optical fiber
15c: photoacoustic wave generation portion
15d: hollow portion
16: optical cable
20: acoustic wave detection unit
21: receiving circuit
22: receiving memory
23: data demultiplexing unit
24: photoacoustic image generation unit
25: ultrasound image generation unit
26: image output unit
27: transmission control circuit
28: control unit
29: sound speed setting unit
30: image display unit
40: input unit
IT: pixel collection portion illustrating tip portion of puncture needle
PT: bright point

What is claimed is:

1. An image generation apparatus comprising:
a processor configured to
generate a photoacoustic image based on a detection signal acquired by detecting a photoacoustic wave emitted from a tip portion of an insert inserted into a subject using an ultrasound probe and a sound speed in the subject; and
extract a region having a predetermined range including a high signal value pixel collection portion having a region size larger than a reference region size as a tip region, which includes the tip portion of the insert, in a photoacoustic image generated based on an assumed sound speed and the detection signal, and set a sound speed of a photoacoustic image having a maximum image evaluation value as the sound speed in the subject among photoacoustic images for respective sound speeds generated by changing the sound speed in a predetermined sound speed range for the tip region, wherein
the processor performs reduction processing of reducing signal intensity of a high signal value pixel collection portion having a region size smaller than the reference region size on the photoacoustic image generated based on an assumed sound speed and the detection signal, and extracts a region having a predetermined range including a pixel having the highest signal value as the tip region in the photoacoustic image subjected to the reduction processing.

2. The image generation apparatus according to claim 1, wherein the image evaluation value is an evaluation value indicating a smallness of intensity variation of a signal phase-adjusted based on sharpness of a photoacoustic image, contrast of the photoacoustic image, or a sound speed at a time of image generation in the tip region.

3. The image generation apparatus according to claim 2, wherein the reference region size is adjusted based on a type of the insert, a generation condition of the photoacoustic wave, a type of the ultrasound probe, frequency characteristics of the ultrasound probe, a reception detection frequency band for the ultrasound probe, or a display size of a photoacoustic image.

4. The image generation apparatus according to claim 2, wherein the processor specifies a high signal value pixel collection portion having a region size larger than the reference region size by image recognition, and extracts a region having a predetermined range including the extracted high signal value pixel collection portion as the tip region.

5. The image generation apparatus according to claim 1, wherein the reference region size is adjusted based on a type of the insert, a generation condition of the photoacoustic wave, a type of the ultrasound probe, frequency characteristics of the ultrasound probe, a reception detection frequency band for the ultrasound probe, or a display size of a photoacoustic image.

6. The image generation apparatus according to claim 5, wherein the processor specifies a high signal value pixel collection portion having a region size larger than the reference region size by image recognition, and extracts a region having a predetermined range including the extracted high signal value pixel collection portion as the tip region.

7. The image generation apparatus according to claim 1, wherein the processor specifies a high signal value pixel collection portion having a region size larger than the reference region size by image recognition, and extracts a region having a predetermined range including the extracted high signal value pixel collection portion as the tip region.

8. The image generation apparatus according to claim 1, wherein the reduction processing is low pass filter processing having a half-width of 0.5 times or more to 2 times or less the reference region size.

9. The image generation apparatus according to claim 1, wherein the reduction processing is smoothing filter processing.

10. The image generation apparatus according to claim 9, wherein in the smoothing filter processing, a smoothing effect in a depth direction is larger than a smoothing effect in a lateral direction in the photoacoustic image.

11. An operation method of an image generation apparatus including a processor that generates a photoacoustic image based on a detection signal acquired by detecting a photoacoustic wave emitted from a tip portion of an insert inserted into a subject using an ultrasound probe and a sound speed in the subject, and the processor sets the sound speed in the subject, the method comprising:
by the processor,
extracting a region having a predetermined range including a high signal value pixel collection portion having a region size larger than a reference region size as a tip region, which includes the tip portion of the insert, in a photoacoustic image generated based on an assumed sound speed and the detection signal; and
setting a sound speed of a photoacoustic image having a maximum image evaluation value as the sound speed in the subject among photoacoustic images for respective sound speeds generated by changing the sound speed in a predetermined sound speed range for the tip region, wherein the processor performs reduction processing of reducing signal intensity of a high signal value pixel collection portion having a region size smaller than the reference region size on the photoacoustic image generated based on an assumed sound speed and the detection signal, and extracts a region having a predetermined range including a pixel having the highest signal value as the tip region in the photoacoustic image subjected to the reduction processing.

12. The operation method according to claim 11, wherein the image evaluation value is an evaluation value indicating a smallness of intensity variation of a signal phase-adjusted based on sharpness of a photoacoustic image, contrast of the photoacoustic image, or a sound speed at a time of image generation in the tip region.

13. The operation method according to claim 11, wherein the reference region size is adjusted based on a type of the insert, a generation condition of the photoacoustic wave, a type of the ultrasound probe, frequency characteristics of the ultrasound probe, a reception detection frequency band for the ultrasound probe, or a display size of a photoacoustic image.

14. The operation method according to claim 11, wherein the processor specifies a high signal value pixel collection portion having a region size larger than the reference region size by image recognition, and extracts a region having a predetermined range including the extracted high signal value pixel collection portion as the tip region.

15. The operation method according to claim 11, wherein the reduction processing is low pass filter processing having a half-width of 0.5 times or more to 2 times or less the reference region size.

16. The operation method according to claim 11, wherein the reduction processing is smoothing filter processing.

17. The operation method according to claim 16, wherein in the smoothing filter processing, a smoothing effect in a depth direction is larger than a smoothing effect in a lateral direction in the photoacoustic image.

* * * * *